United States Patent [19]

Imuta et al.

[11] Patent Number: 5,338,733
[45] Date of Patent: Aug. 16, 1994

[54] ISOXAZOLIDINYL CARBAPENEM DERIVATIVE

[75] Inventors: Mitsuru Imuta, Neyagawa; Koichi Nishi, Nara, both of Japan

[73] Assignee: Shionogi Seiyaku Kabushiki Kaisha, Osaka, Japan

[21] Appl. No.: 39,957

[22] Filed: Mar. 30, 1993

[30] Foreign Application Priority Data

Apr. 1, 1992 [JP] Japan .................................. 4-080065

[51] Int. Cl.$^5$ .................. C07D 487/00; A01N 43/00; A61K 31/395
[52] U.S. Cl. ...................................... 514/210; 540/302
[58] Field of Search .......................... 540/302; 514/210

[56] References Cited

U.S. PATENT DOCUMENTS

| | | | |
|---|---|---|---|
| 4,833,167 | 5/1989 | Christensen et al. | 540/302 |
| 4,933,333 | 6/1990 | Sunagawa et al. | 514/192 |
| 4,943,569 | 7/1990 | Sunagawa | 514/210 |
| 5,122,604 | 6/1992 | Sunagawa et al. | 540/350 |

FOREIGN PATENT DOCUMENTS

| | | |
|---|---|---|
| 1283906 | 5/1991 | Canada . |
| 0010316 | 4/1980 | European Pat. Off. . |
| 0030032 | 6/1981 | European Pat. Off. . |
| 0111286 | 6/1984 | European Pat. Off. . |
| 0394991 | 10/1990 | European Pat. Off. . |
| 3232891 | 10/1991 | Japan . |

*Primary Examiner*—Johann Richter
*Assistant Examiner*—Rebecca Cook
*Attorney, Agent, or Firm*—Renner, Otto, Boisselle & Sklar

[57] ABSTRACT

A carbapenem derivative represented by Formula I:

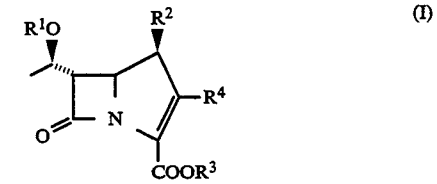

wherein $R^1$ is hydrogen or a hydroxy protecting group; $R^2$ is substituted or non-substituted lower alkyl; $R^3$ is hydrogen, an inorganic or organic base, or a carboxy protecting group; and $R^4$ is a compound represented by any of the following Formulae II through V:

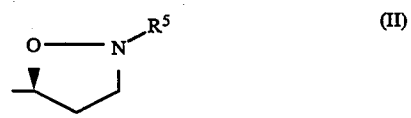

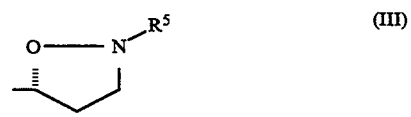

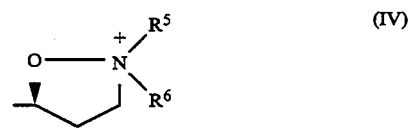

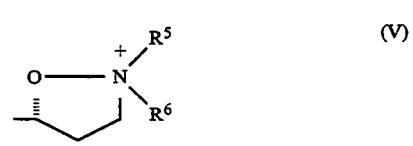

wherein $R^5$ and $R^6$ are independently substituted or non-substituted lower alkyl.

16 Claims, No Drawings

ISOXAZOLIDINYL CARBAPENEM DERIVATIVE

BACKGROUND OF THE INVENTION

1. Field of the Invention

The present invention relates to a novel carbapenem derivative having a wide range of antibacterial spectrum, a method for producing the same, an antibacterial agent or a therapeutic agent for sensitive bacteria containing the carbapenem derivative as an effective ingredient, and a method for combating bacteria by utilizing the carbapenem derivative.

2. Description of the Related Art

Various compounds are known as carbapenems, a kind of a β-lactam antibiotic. For example, imipenem, meropenem, the mesylate, and the urea derivatives of a carbapenem as shown below are known (Japanese Laid-Open Patent Publication Nos. 60-19787 and 60-233076).

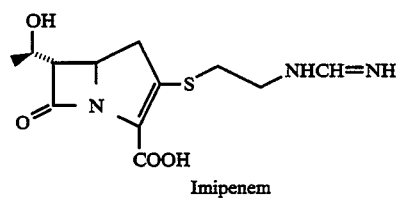
Imipenem

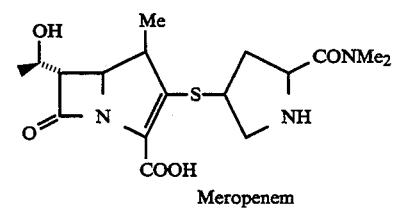
Meropenem

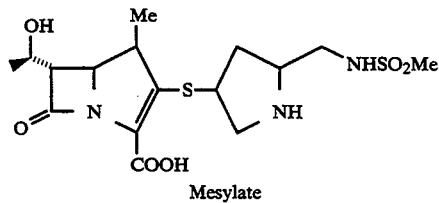
Mesylate

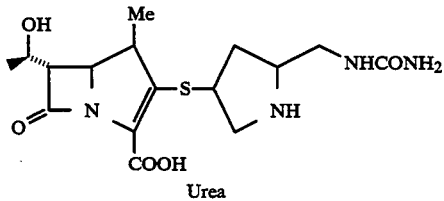
Urea

E.P.A. No. 30032 discloses a 2-cycloalkylcarbapenem derivative. E.P.A. No. 394991 discloses a carbapenem derivative which has a non-aromatic heterocycle having a nitrogen atom at the 2-position of the carbapenem skeleton. These are carbapenem derivatives having a ring at the 2-position of the carbapenem skeleton.

All of these carbapenem compounds have a wide range of antibacterial spectrum, and are effective against Gram-positive bacteria, Gram-negative bacteria and various kinds of resistant strains.

SUMMARY OF THE INVENTION

The carbapenem derivative of this invention is represented by Formula I:

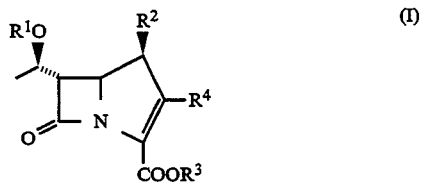

wherein $R^1$ is hydrogen or a hydroxy protecting group; $R^2$ is substituted or non-substituted lower alkyl; $R^3$ is hydrogen, an inorganic or organic base, or a carboxy protecting group; and $R^4$ is a group represented by any of the following Formulae II through V:

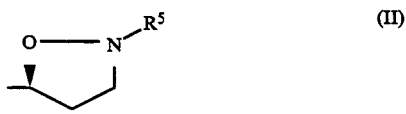

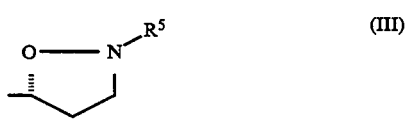

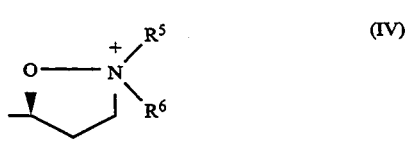

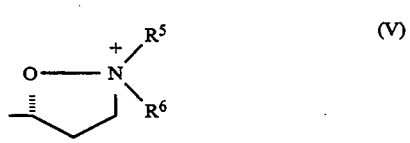

wherein $R^5$ and $R^6$ are independently substituted or non-substituted lower alkyl.

Alternatively, in the above Formula I, $R^1$ is hydrogen; $R^2$ is methyl; $R^3$ is hydrogen, an inorganic or organic base, or a carboxy protecting group; and $R^4$ is a group represented by any of the following Formulae IIa, IIIa, IVa and Va:

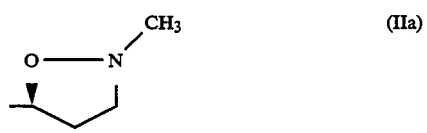

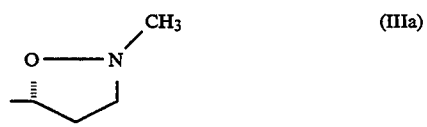

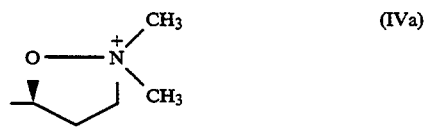

-continued

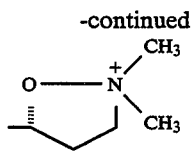
(Va)

Alternatively, the method for producing a carbapenem derivative of the present invention comprises the steps of:

substituting hydroxy of a carbapenem derivative represented by Formula VI with halogen, the halogen then being converted into phosphonium salt to obtain a carbapenem derivative represented by Formula VII:

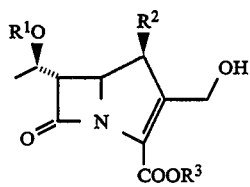
(VI)

wherein $R^1$ is hydrogen or a hydroxy protecting group; $R^2$ is substituted or non-substituted lower alkyl; and $R^3$ is hydrogen, an inorganic or organic base, or a carboxy protecting group;

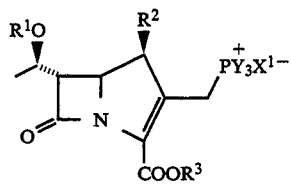
(VII)

wherein $R^1$ is hydrogen or a hydroxy protecting group; $R^2$ is substituted or non-substituted lower alkyl; $R^3$ is hydrogen, an inorganic or organic base, or a carboxy protecting group; $X^1$ is halogen; and Y is alkyl or aryl;

converting the carbapenem derivative represented by Formula VII into a carbapenem derivative represented by Formula VIII by the Wittig reaction:

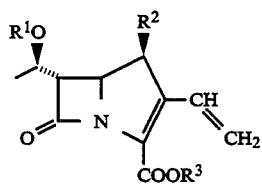
(VIII)

wherein $R^1$ is hydrogen or a hydroxy protecting group; $R^2$ is substituted or non-substituted lower alkyl; and $R^3$ is hydrogen, an inorganic or organic base, or a carboxy protecting group; and reacting the carbapenem derivative represented by Formula VIII with formaldehyde and hydroxylamine represented by $R^5$NHOH, wherein $R^5$ is substituted or non-substituted lower alkyl, to give an isoxazolidinyl carbapenem derivative represented by Formula I-1:

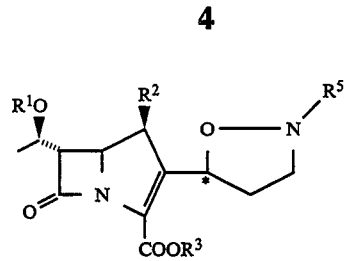
(I-1)

wherein $R^1$ is hydrogen or a hydroxy protecting group; $R^2$ is substituted or non-substituted lower alkyl; $R^3$ is hydrogen, an inorganic or organic base, or a carboxy protecting group; $R^5$ is substituted or non-substituted lower alkyl; and a configuration of a carbon atom marked with * is R or S.

Alternatively, the method for producing a carbapenem derivative of the present invention comprises the steps of:

substituting hydroxy of a carbapenem derivative represented by Formula VI with halogen, the halogen then being converted into phosphonium salt to obtain a carbapenem derivative represented by Formula VII:

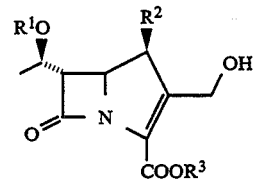
(VI)

wherein $R^1$ is hydrogen or a hydroxy protecting group; $R^2$ is substituted or non-substituted lower alkyl; and $R^3$ is hydrogen, an inorganic or organic base, or a carboxy protecting group;

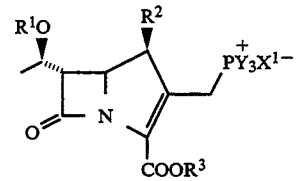
(VII)

wherein $R^1$ is hydrogen or a hydroxy protecting group; $R^2$ is substituted or non-substituted lower alkyl; $R^3$ is hydrogen, an inorganic or organic base, or a carboxy protecting group; $X^1$ is halogen; and Y is alkyl or aryl;

converting the carbapenem derivative represented by Formula VII into a carbapenem derivative represented by Formula VIII by the Wittig reaction:

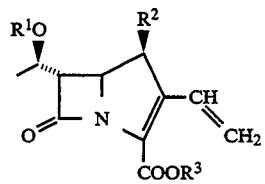
(VIII)

wherein $R^1$ is hydrogen or a hydroxy protecting group; $R^2$ is substituted or non-substituted lower alkyl; and $R^3$ is hydrogen, an inorganic or organic base, or carboxy protecting group;

reacting the carbapenem derivative represented by Formula VIII with formaldehyde and hydroxylamine represented by $R^5NHOH$, wherein $R^5$ is substituted or non-substituted lower alkyl, to give an isoxazolidinyl carbapenem derivative represented by Formula I-1:

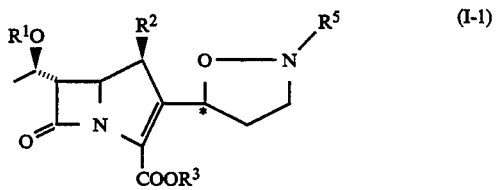

wherein $R^1$ is hydrogen or a hydroxy protecting group; $R^2$ is substituted or non-substituted lower alkyl; $R^3$ is hydrogen, an inorganic or organic base, or a carboxy protecting group; $R^5$ is substituted or non-substituted lower alkyl; and a configuration of a carbon atom marked with * is R or S; and reacting the isoxazolidinyl carbapenem derivative represented by Formula I-1 with alkylated halogen represented by $R^6X^2$, wherein $R^6$ is substituted or non-substituted lower alkyl and $X^2$ is halogen, to give an isoxazolidinium carbapenem derivative represented by I-2:

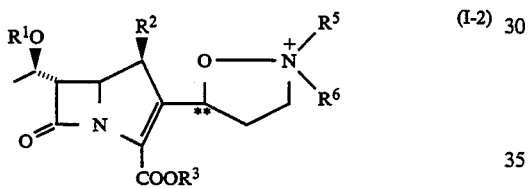

wherein $R^1$ is hydrogen or a hydroxy protecting group; $R^2$ is substituted or non-substituted lower alkyl; $R^3$ is hydrogen, an inorganic or organic base, or a carboxy protecting group $R^5$ and $R^6$ are independently substituted or non-substituted lower alkyl; and a configuration of a carbon atom marked with ** is R or S.

Alternatively, the present invention provides an antibacterial agent comprising the above-mentioned carbapenem derivative as an active ingredient.

Alternatively, the present invention provides a therapeutic agent for sensitive bacterial infection comprising the above-mentioned carbapenem derivative as an active ingredient.

Alternatively, the present invention provides a method for combating bacteria sensitive to the carbapenem derivative by allowing the sensitive bacterium to be in contact with a bacteriostatically effective amount of the carbapenem derivative.

Thus, the invention described herein makes possible the advantages of (1) providing a carbapenem derivative having a strong antibacterial force and a wide range of antibacterial spectrum, and a method for producing the same; (2) providing a carbapenem derivative which has a low hydrolysis rate in the body for maintaining its effect for a long time; (3) providing an antibacterial agent or a therapeutic agent for sensitive microbism comprising the above-mentioned carbapenem derivative as an effective ingredient; and (4) providing a sterilization method or a bacteriostasis method utilizing the above-mentioned carbapenem derivative.

These and other advantages of the present invention will become apparent to those skilled in the art upon reading and understanding the following detailed description.

DESCRIPTION OF THE PREFERRED EMBODIMENTS

The present invention will now be described in detail.

A carbapenem derivative of the present invention is represented by the following Formula I:

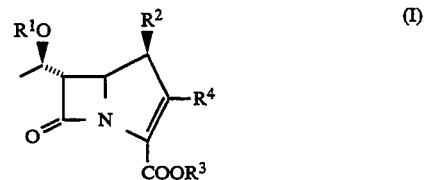

wherein $R^1$ is hydrogen or a hydroxy protecting group; $R^2$ is substituted or non-substituted lower alkyl; $R^3$ is hydrogen, an organic or an inorganic base, or a carboxy protecting group; and $R^4$ is a compound represented by any of the following Formulae II through V:

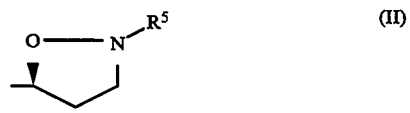

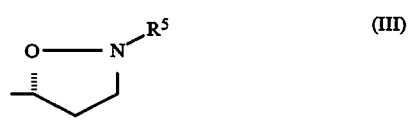

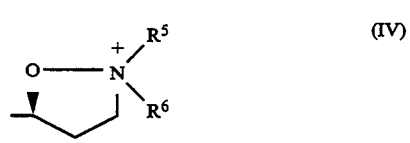

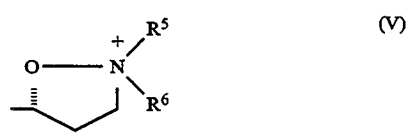

wherein $R^5$ and $R^6$ are independently substituted or non-substituted lower alkyl.

The carbapenem derivative of the present invention is a compound represented by the following Formula I-1 or I-2, in which a 5-isoxazolidinyl group or a 5-isoxazolidinium group is at the 2-position of the carbapenem skeleton:

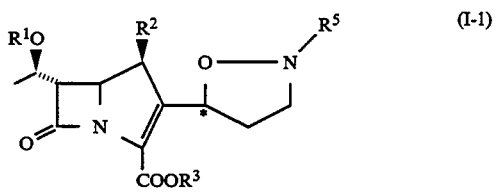

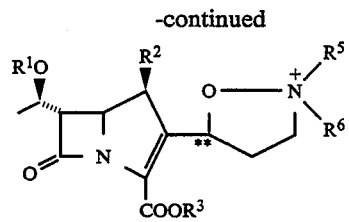
(I-2)

A preferred scope of each group herein is as follows:

The number of carbon atoms of "lower alkyl" is 1 to 6. Examples of such an alkyl group include methyl, ethyl, n-propyl, iso-propyl, n-butyl, t-butyl, pentyl and hexyl. The number of carbon atoms of the lower alkyl is preferably 1 to 4. The most preferred lower alkyl is methyl or ethyl. Examples of the substituent of substituted lower alkyl include hydroxy, alkoxy, amino, acylamino, lower alkylamino, carbamoyl, lower alkylcarbamoyl, carbamoyloxy, lower alkylcarbamoyloxy and cyano.

Examples of the "hydroxy protecting group" include lower alkoxycarbonyl such as t-butyloxycarbonyl; halogenoalkoxycarbonyl such as 2-iodoethyl oxycarbonyl, and 2,2,2-trichloroethyloxycarbonyl; aralkyloxycarbonyl such as benzyloxycarbonyl, p-methoxybenzyloxycarbonyl, o-nitrobenzyloxycarbonyl and p-nitrobenzyloxycarbonyl; and trialkylsilyl such as trimethylsilyl, triethylsilyl, and t-butyldimethylsilyl.

Examples of the "carboxy protecting group" include lower alkyl; lower alkanyl such as allyl, isopentenyl and 2-butenyl; halogeno lower alkyl such as 2-iodoethyl and 2,2,2-trichloroethyl; lower alkoxymethyl such as methoxymethyl, ethoxymethyl and isobuthoxymethyl; lower aliphatic acyloxymethyl such as acetoxymethyl, propionyloxy, butyryloxymethyl and pivaloyloxymethyl; 1-lower alkoxycarbonyloxyethyl such as 1-methoxycarbonyloxyethyl and 1-ethoxycarbonyloxyethyl; aralkyl such as benzyl, p-methoxybenzyl, o-nitrobenzyl, p-nitrobenzyl and diphenylmethyl; benzhydryl; and phthalidyl.

In the carbapanem derivative of the present invention, the configuration of the carbon atoms at the 1-position and the 6-position in the carbapenem skeleton is S.

Therefore, the preferred carbapenem derivatives of the present invention are exemplified as follows:

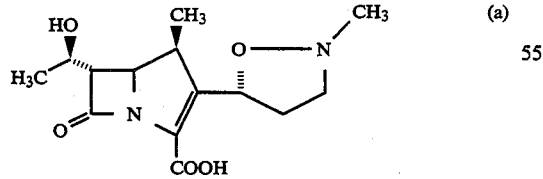
(a)

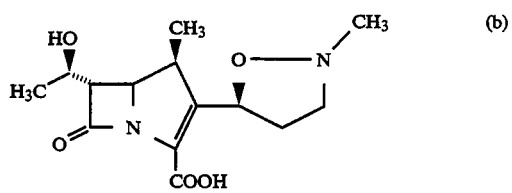
(b)

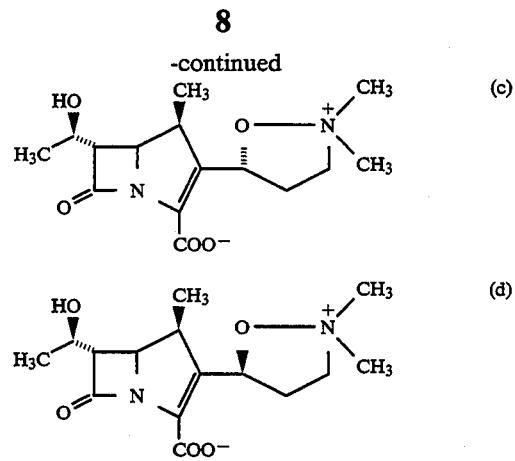

The carbapenem derivative of the present invention includes pharmaceutically acceptable salts thereof. Examples of the pharmaceutically acceptable salts include a salt with a base, a salt with an acid, a salt with a basic or acidic amino acid and an intermolecular or intramolecular quarternary salt. The intramolecular quarternary salts include, for example, the above-mentioned compounds (c) and (d). Examples of the salt with a base include inorganic base addition salts such as alkali metal salts (e.g. sodium salt and potassium salt), alkaline-earth metal salts (e.g. calcium salt and magnesium salt), and ammonium salt; and organic base addition salts such as triethylamine salt, pyridine salt, picoline salt, ethanolamine salt, triethanolamine salt, dicyclohexylamine salt, N,N'-dibenzylethylenediamine salt and dibenzylamine salt. Examples of the salt with an acid include inorganic acid addition salts such as hydrochloride, hydrobromide, sulfuric acid salt and phosphoric acid salt; and organic acid addition salts such as formic acid salt, acetic acid salt, trifluoroacetic acid salt, maleic acid salt, tartaric acid salt, methanesulfonic acid salt, benzenesulfonic acid salt and toluenesulfonic acid salt. Examples of the salt with an amino acid include a salt with arginine, lysine, aspartic acid or glutamic acid.

A production method for the carbapenem derivative will now be described.

A hydroxyl group of a carbapenem derivative represented by the following Formula VI is substituted with halogen, which is then converted into phosphonium salt, thereby obtaining a carbapenem derivative represented by the following Formula VII:

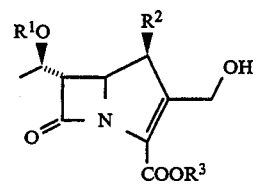
(VI)

wherein $R^1$, $R^2$ and $R^3$ are respectively the same as defined in Formula I;

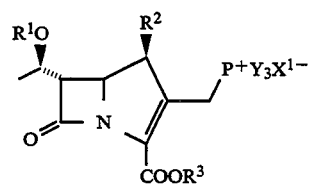
(VII)

wherein $R^1$, $R^2$ and $R^3$ are respectively the same as defined in Formula I, $X^1$ is halogen, and Y is alkyl or aryl.

For example, by reacting the carbapenem derivative VI with halogen and either triarylphosphine or trialkylphosphine in the presence of a base, the hydroxyl group of the carbapenem derivative VI is halogenated. Then, the resultant halogen substituted carbapenem derivative is allowed to react with either triarylphosphine or trialkylphosphine to give the carbapenem derivative VII.

In the above-mentioned halogenation reaction of the hydroxyl group of the carbapenem derivative VI, the carbapenem derivative VI together with triarylphosphine or trialkylphosphine forms a complex, which is then allowed to react with halogen. As the halogen, iodine is preferable. An example of the triarylphosphine includes triphenylphosphine, and an example of the trialkylphosphine includes triethylphosphine, among which triphenylphosphine is most preferable.

The amount of the halogen to be used in the above described reaction is preferably 1 to 1.5 equivalents of the carbapenem derivative VI, and the amount of the triarylphosphine or trialkylphosphine used in the reaction is preferably 1 to 1.5 equivalents of the carbapenem derivative VI.

Examples of the base to be used in the reaction include organic bases such as trimethylamine, triethylamine, pyridine and diisopropylethylamine; and inorganic bases such as potassium carbonate, sodium carbonate and sodium hydrogencarbonate, among which triethylamine is preferable. The amount of the base is preferably 1 to 1.5 equivalents of the carbapenem derivative VI.

Examples of the solvent to be used include dichloromethane and chloroform, among which dichloromethane is preferable.

It is preferable to use a non-protic polar solvent such as dimethyl formamide, dimethyl sulphoxide and hexamethyl phosphoroamide in order to accelerate the above-mentioned reaction.

The reaction is generally conducted at a temperature of −50° to −30° C. for 0.5 to 1 hour.

The resultant halogen substituted carbapenem derivative can be used in the subsequent step without being isolated, i.e., in the form of a reaction liquid.

In the above reaction for obtaining the carbapenem derivative VII from the compound obtained by the halogenation of hydroxy of the carbapenem derivative VI, the amount of the used triarylphosphine or trialkylphosphine is preferably 1 to 1.5 equivalents of the carbapenem derivative VI.

The triarylphosphine or trialkylphosphine, and the solvent used in the reaction can be identical to those used in the above-mentioned halogenation reaction.

The reaction is generally conducted at a temperature of −20° to 0° C. for 3 to 6 hours.

Next, the carbapenem derivative VII is converted into a carbapenem derivative represented by the following Formula VIII by the Wittig reaction:

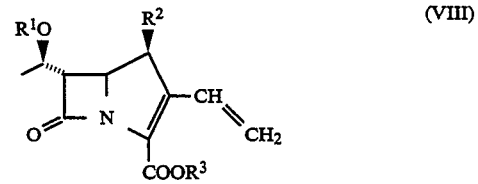

wherein $R^1$, $R^2$ and $R^3$ are respectively the same as defined in Formula I.

Namely, the carbapenem derivative VII is allowed to react with formaldehyde in the presence of a base to obtain the carbapenem derivative VIII.

The amount of the formaldehyde to be used in the reaction is preferably 10 to 20 equivalents of the carbapenem derivative VII. Examples of the base include organic bases such as trimethylamine, triethylamine and pyridine; and inorganic bases such as potassium carbonate, sodium carbonate and sodium hydrogencarbonate, among which sodium carbonate is preferred. The amount of the base to be used in the reaction is preferably 1 to 2 equivalents of the carbapenem derivative VII.

Examples of the solvent to be used include dichloromethane, chloroform, toluene and benzene, among which toluene is preferred.

The reaction is generally conducted at a temperature of 15° to 25° C. for 0.5 to 1 hour.

Next, the carbapenem derivative VIII is allowed to react with hydroxylamine represented by a general formula $R^5$NHOH (wherein $R^5$ is the same as defined above) and formaldehyde to give an isoxazolidinyl carbapenem derivative represented by the following Formula I-1:

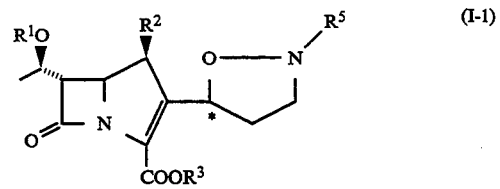

wherein $R^1$, $R^2$, $R^3$ and $R^5$ are respectively the same as defined in Formula I or II; and the configuration of the carbon atom marked with * is R or S.

The amount of the hydroxylamine to be used in the reaction is preferably 1.5 to 3 equivalents of the carbapenem derivative VIII, and the amount of the formaldehyde is preferably 10 to 20 equivalents of the carbapenem derivative VIII. Examples of the solvent to be used include dioxane, tetrahydrofuran, methanol, ethanol, dimethylformamide, dimethylsulphoxide, acetone and acetonitrile.

The reaction is generally conducted at a temperature of 80° to 110° C. for 2 to 4 hours.

Next, the isoxazolidinyl carbapenem derivative I-1 is allowed to react with alkylated halogen represented by a general formula $R^6X^2$ (wherein $R^6$ is the same as defined above and $X^2$ is halogen), thereby converting the nitrogen atom of the isoxazolidinyl group into quaternary alkyl to obtain an isoxazolidinium carbapenem derivative represented by the following Formula I-2:

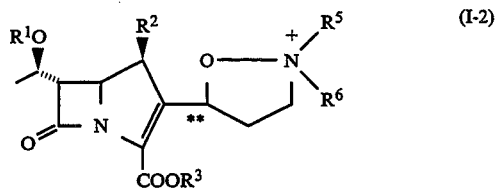

(I-2)

wherein R¹, R², R³, R⁵ and R⁶ are respectively the same as defined in Formula I or IV; and the configuration of the carbon atom marked with ** is R or S.

The amount of the halogenated alkyl used in the above-mentioned reaction is preferably 2 to 5 equivalents of the isoxazolidinyl carbapenem derivative I-1.

Examples of the solvent to be used include dichloromethane and acetonitrile, among which acetonitrile is preferable.

The reaction is generally conducted at a temperature of 15° to 25° C. for 10 to 30 minutes.

The isoxazolidinyl carbapenem derivative I-1 and the isoxazolidinium carbapenem derivative I-2 having a protecting group can be deprotected, if necessary. For example, a carboxy protecting group such as p-methoxybenzyl can be deprotected by reacting with an acid such as AlCl₃, BF₃, TiCl₄ and trifluoro acetic acid. A hydroxy protecting group such as trimethylsilyl can be deprotected by reacting with an acid such as AlCl₃ and hydrochloric acid.

As an antibiotic having groups similar to those of the carbapenem derivative of the present invention, Japanese Laid-Open Patent Publication No. 3-232891 discloses cephalosporin derivatives represented by the following formulae:

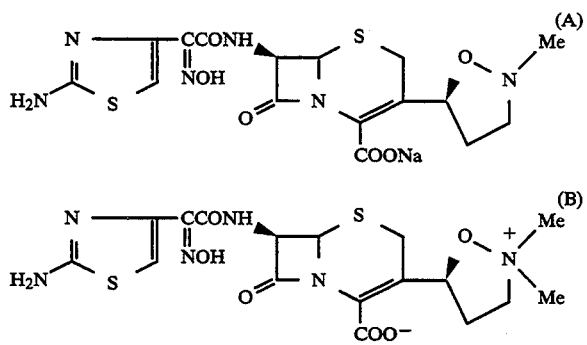

These cephalosporin derivatives have a wide range of antibacterial spectrum, and are effective against Gram-positive bacteria, Gram-negative bacteria and various kinds of resistant strains. However, as is apparent from the examples described below, the cephalosporins have a lower antibacterial activity against Gram-positive bacteria, Gram-negative bacteria and various kinds of resistant strains than the carbapenem derivative of the present invention.

A pharmaceutical composition comprising the carbapenem derivative (including pharmaceutically acceptable salts thereof) as an effective ingredient is administered as an antibacterial agent. An administration method is in oral administration or parenteral administration; as injection (a formulation in an ampoule or vial, a liquid, a suspension or the like for an intravenous injection, an intramuscular injection, a drip infusion, or subcutaneous injection), an external or local administration agent (an ear drop, a nasal drop, an ophthalmic solution, an ointment, an emulsion, a spray, a suppository and the like), and an oral preparation. Preferably, the composition is administered by injection, through skin or mucose. The preparation comprises 98% by weight or more of the carbapenem derivative, and further includes an appropriate excipient, auxiliary agent, stabilizer, wetting agent, emulsifier, and other additives depending upon the administration method. These additives must be pharmaceutically and pharmacologically acceptable materials which do not inhibit the effect of the carbapenem derivative of the present invention. For example, lactose, stearic acid, magnesium stearate, clay, sucrose, cornstarch, talc, gelatin, agar, pectin, peanut oil, olive oil, cacao oil, ethylene glycol, tartaric acid, citric acid and fumaric acid can be contained in the oral preparation. For parenteral administration, a solvent (e.g. alcohol, a buffer, methyl oleate, water or the like), a buffer solution, a dispersing agent, a dissolving auxiliary agent, a stabilizer (e.g. methyl p-hydroxybenzoate, ethyl p-hydroxybenzoate, sorbic acid or the like), an absorbefacient (mono- or dioctanoate of glycerin), an antioxidant, a perfume, an analgetic, a dispersing agent, an adverse effect inhibitor, an action potentiator (an agent for regulating absorption and elimination, an inhibitor for enzyme decomposition, a β-lactamase inhibitor, and other kinds of antimicrobial agents) and the like can be contained in the formulation.

A dose of the carbapenem derivative of the present invention depends upon the age of a patient, the type and the state of the disease and the kind of compounds to be used. Generally, daily dose ranges from 500 mg/patient to 1000 mg/patient in the internal application, but more can be administered if necessary. The carbapenem derivative of the present invention can be used in a therapeutic agent for sensitive bacterial infection since it can combat bacteria by coming in contact with them. For example, a dose of 1000 mg (intravenous injection) is administered 2 to 4 times a day to treat an infection.

The present invention will now be described by way of examples.

EXAMPLE 1

Step 1. Preparation of
(1S,6S)-2-iodomethyl-1-methyl-6-((R)-1-triethylsilyloxyethyl)-1-carba-2-penem-3-carboxylic acid p-methoxybenzyl ester

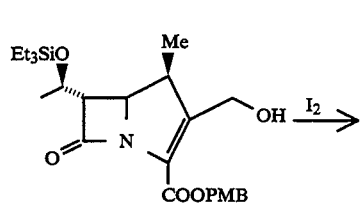

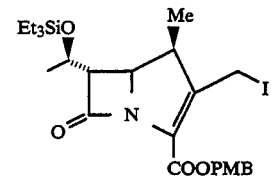

A solution of (1S,6S)-2-hydroxymethyl-1-methyl-6-((R)-1-triethylsilyloxyethyl)-1-carba-2-penem-3-carboxylic acid p-methoxybenzyl ester (43.68 g; 0.092 mol)

in dichloromethane (100 ml) was cooled to about −50° C., triethylamine (14.1 ml; 1.1 eq.), iodine (25.64 g; 1.1 eq.) and triphenylphosphine (36.13 g; 1.5 eq.) were successively added thereto, and the mixture was stirred for about 1 hour. Hexamethylphosphoramide (32 ml; 2 eq.) was further added thereto at about −50° C., and the resultant mixture was stirred for about 30 minutes to give a solution of (1S,6S)-2-iodomethyl-1-methyl-6-((R)-1-triethylsilyloxyethyl)-1-carba-2-penem-3-carboxylic acid p-methoxybenzyl ester.

Step 2. Preparation of an iodide of (1S,6S)-1-methyl-6-((R)-1-triethylsilyloxyethyl)-2-triphenylphosphoniomethyl-1-carba-2-penem-3-carboxylic acid p-methoxybenzyl ester

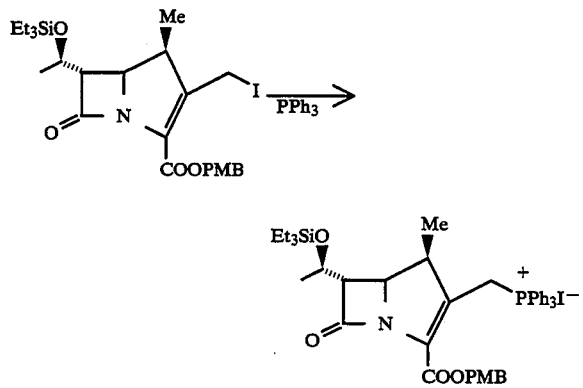

The solution of (1S,6S)-2-iodomethyl-1-methyl-6-((R)-1-triethylsilyloxyethyl)-1-carba-2-penem-3-carboxylic acid p-methoxybenzyl ester obtained in Step 1 in dichloromethene was cooled to −20° C., and triphenylphosphine (24.09 g; 1 eq.) was added thereto. The resultant solution was allowed to stand overnight at −20° C. The reaction solution was poured into cold water-ethyl acetate, the organic layer was separated, and the aqueous layer was extracted with ethyl acetate. The ethyl acetate layer was combined, washed with water, dried over magnesium sulfate, end concentrated in vacuo. The residue was powdered with ether and washed to give a crude iodide of (1S,6S)-1-methyl-6-((R)-1-triethylsilyloxyethyl)-2-triphenylphosphoniomethyl-1-carba-2-penem-3-carboxylic acid p-methoxybenzyl ester (85.57 g). Total yield from Step 1: 100%. Purity: 91%.

$^1$H-NMR(CDCl$_3$) δ:0.55 (q, J=7.8 Hz, 6H), 0.90 (t, J=7.8 Hz, 9H), 1.17 (d, J=6.2 Hz, 3H), 1.35 (d, J=7.2 Hz, 3H), 2.65-2.90 (m, 1H), 3.23 (dd, J=4.6 Hz, 3.0 Hz, 1H), 3.82 (s, 3H), 4.06 (dd, J=10.2 Hz, 3.0 Hz, 1H), 4.22 (dq, J=6.2 Hz, 4.6 Hz, 1H), 4.77 (s, 2H), 5.19 (t-like, J=15.6 Hz, 1H), 5.45 (t-like, J=15.0 Hz, 1H), 6.86 (d, J=8.8 Hz, 2H), 7.18 (d, J=8.8 Hz, 2H), 7.41-7.87 (m, 15H)

IR ν max (CHCl$_3$) cm$^{-1}$: 1778, 1709 MS m/z: 720[(M−I)$^+$], 1567[(2M−I)$^+$] [(M−I)$^+$] C$_{43}$H$_{51}$NO$_5$PSi Calcd.: 720.3272 Found: 720.3286

Step 3. Preparation of (1S,6S)-1-methyl-6-((R)-1-triethylsilyloxyethyl)-2-vinyl-1-carba-2-penem-3carboxylic acid p-methoxybenzyl ester

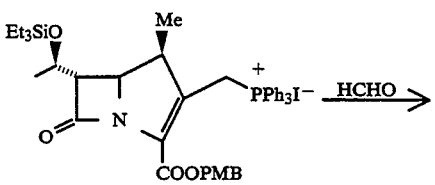

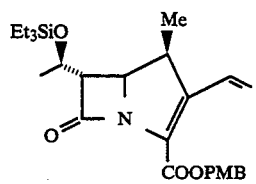

The iodide of (1S,6S)-1-methyl-6-((R)-1-triethylsilyloxyethyl)-2-triphenylphosphoniomethyl-1-carba-2-penem-3-carboxylic acid p-methoxybenzyl ester (37.23 g; 39.97 mmol; purity: 91%) obtained in Step 2 was dissolved in a mixture of toluene (400 ml), dichloromethane (20 ml) and water (200 ml). An aqueous solution of 37% formalin (71.3 ml; 22 eq.) and sodium carbonate (6.98 g; 1.65 eq.) were added to the resultant solution, and the mixture was stirred for about 1 hour at room temperature. The reaction mixture was poured into water-ethyl acetate, the organic layer was separated, and the aqueous layer was extracted with ethyl acetate. The ethyl acetate layer was combined, washed with water end saturated brine, dried over magnesium sulfate end concentrated in vacuo. The residue was purified by a silica gel column chromatography (toluene:ethyl acetate=20:1) to give (1S,6S)-1-methyl-6-((R)-1-triethylsilyloxyethyl)-2-vinyl-1-carba-2-penem-3-carboxylic acid p-methoxybenzyl ester (12 g). Yield: 64%.

$^1$H-NMR(CDCl$_3$) δ:0.59 (q, J=8.0 Hz, 6H), 0.94 (t, J=8.0 Hz, 9H), 1.20 (d, J=7.6 Hz, 3H), 1.29 (d, J=6.0 Hz, 3H), 3.19 (dd, J=6.7 Hz, 2.6 Hz, 1H), 3.35 (quint, J=7.6 Hz, 1H), 3.80 (s, 3H), 4.12 (dd, J=9.4 Hz, 2.6 Hz, 1H), 4.22 (quint, J=6.4 Hz, 1H), 5.23 (s, 2H), 5.43 (dd, J=11.2 Hz, 0.9 Hz, 1H), 5.50 (dd, J=18.0 Hz, 0.9 Hz, 1H), 6.88 (d, J=8.7 Hz, 2H), 7.34 (dd, J=18.0 Hz, 11.2 Hz, 1H), 7.39 (d, J=8.7 Hz, 2H)

IR ν max (CHCl$_3$) cm$^{-1}$: 1760, 1708 MS m/z: 472[(M+H)$^+$], 943[(2M+H)$^+$] [(M+H)$^+$] C$_{26}$H$_{38}$NO$_5$Si Calcd.: 472.2518 Found: 472.2525

Step 4. Preparation of (1S,6S)-1-methyl-2-((5R)-2-methylisoxazolidine-5-yl)-6-((R)-1-triethylsilyloxyethyl)-1-carba-2-penem-3-carboxylic acid p-methoxybenzyl ester and (1S,6S)-1-methyl-2-((5S)-2-methylisoxazolidine-5-yl)-6-((R)-1-triethylsilyloxyethyl)-1-carba-2-penem-3-carboxylic acid p-methoxybenzyl ester

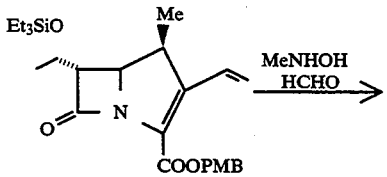

-continued

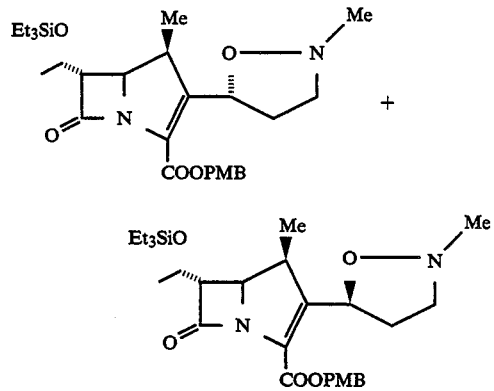

The (1S,6S)-1-methyl-6-((R)-1-triethylsilyloxyethyl)-2-vinyl-1-carba-2-penem-3-carboxylic acid p-methoxybenzyl ester (6.24 g; 13.2 mmol) was dissolved in 100 ml of toluene. Separately, N-methylhydroxylamine hydrochloride (3.32 g; 3 eq.) was dissolved in 40 ml of sodium methoxide.(1M/MeOH; 3.1 eq.). Twenty-four ml of an aqueous solution of 37% formalin was added to the latter mixture at room temperature. The resultant aqueous solution was added to the former toluene solution, and the mixture was heated at 110° C. for 4 hours. Then, the mixture was cooled, diluted with water (50 ml), and extracted with ether (200 ml). The extract was concentrated, and purified by the silica gel column chromatography (toluene:ethyl acetate=3:1) to give (1S,6S)-1-methyl-2-((5R)-2-methylisoxszolidine-5-yl)-6-((R)-1-triethylsilyloxyethyl)-1-carba-2-penem-3-carboxylic acid p-methoxybenzyl ester (962 mg; Yield: 22%) with a low polarity and an isomer thereof with a high polarity, that is, (1S,6S)-1-methyl-2-((5S)-2-methylisoxazolidine-5-yl)-6-((R)-1-triethylsiyloxyethyl)-1-carba-2-penem-3-carboxylic acid p-methoxybenzyl ester (1.97 g; Yield: 45%).

<The 5R compound with a low polarity>

$^1$H-NMR (CDCl$_3$ ) δ:0.58 (g, J=7.8 Hz, 6H), 0.94 (t, J=7.8 Hz, 9H), 1.23 (d, J=7.0 Hz, 3H), 1.26 (d, J=6.0 Hz, 3H), 1.88–2.14 (m, 1H), 2.39–2.58 (m, 1H), 2.60–2.86 (m, 1H), 2.67 (s, 3H), 3.10–3.45 (m, 2H), 3.18 (dd, J=6.6 Hz, 2.4 Hz, 1H), 3.80 (s, 3H), 4.06 (dd, J=9.3 Hz, 2.4 Hz, 1H), 4.20 (quint, J=6.3 Hz, 1H), 5.15 (ABq, J=12.3 Hz, 1H), 5.23 (ABq, J=12.3 Hz, 1H), 5.43–5.62 (m, 1H), 6.88 (d, J=8.8 Hz, 2H), 7.38 (d, J=8.8 Hz, 2H)

IR ν max (CHCl$_3$) cm$^{-1}$: 1763, 1709 MS m/z: 531[(M+H)$^+$] [(M+H)$^+$] C$_{28}$H$_{43}$N$_2$O$_6$Si Calcd.: 531.2888 Found: 531.2894

<The 5S compound with a high polarity>

$^1$H-NMR (CDCl$_3$) δ:0.58 (q, J=7.8 Hz, 6H), 0.94 (t, J=7.8 Hz, 9H), 1.23 (d, J=7.4 Hz, 3H), 1.27 (d, J=6.0 Hz, 3H), 1.27–2.09 (m, 1H), 2.22–2.48 (m, 1H), 2.56–2.89 (m, 1H), 2.66 (s, 3H), 3.15–3.58 (m, 2H), 3.20 (dd, J=7.0 Hz, 2.8 Hz, 1H), 3.80 (s, 3H), 4.09 (dd, J=9.9 Hz, 2.8 Hz, 1H), 4.19 (quint, J=6.4 Hz, 1H), 5.19 (s, 2H), 5.34–5.55 (m, 1H), 6.88 (d, J=8.8 Hz, 2H), 7.37 (d, J=8.8 Hz, 2H)

IR ν max (CHCl$_3$) cm$^{-1}$: 1764, 1709 MS m/z: 531[(M+H)$^+$] [(M+H)$^+$] C$_{28}$H$_{43}$N$_2$O$_6$Si Calcd.: 531.2888 Found: 531,2890

EXAMPLE 2

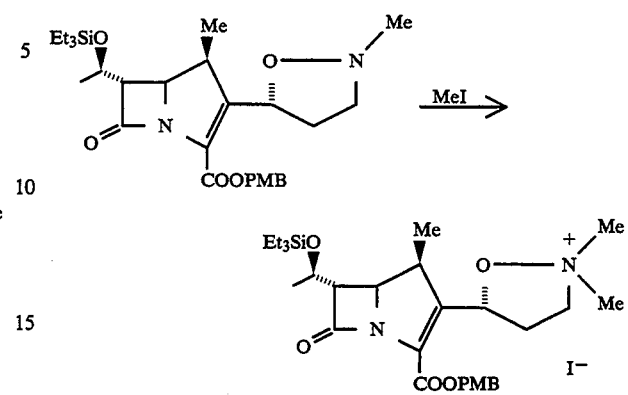

To a solution of the (1S,6S)-1-methyl-2-((5R)-2-methylisoxazolidine-5-yl)-6-((R)-1-triethylsilyloxethyl)-1-carba-2-penem-3-carboxylic acid p-methoxybenzyl ester (839 mg; 1.58 mmol) obtained in Example 1 in acetonitrile (10 ml) was added iodomethane (10 ml) at room temperature. The resultant solution was stirred for about 10 minutes and concentrated in vacuo to give a crude iodide of (1S,6S)-2-((5R)-2,2-dimethylisoxazolidinio-5-yl)-1-methyl-6-((R)-1-triethylsilyloxyethyl)-1-carba-2-penem-3-carboxylic acid p-methoxybenzyl ester (1.13 g). Yield: 100%. Purity: 94%.

$^1$H-NMR (CDCl$_3$) δ:0.58 (q, J=8.0 Hz, 6H), 0. 93 (t, J=8.0 Hz, 9H), 1.20 (d, J=7.2 Hz, 3H), 1.23 (d, J=6.2 Hz, 3H), 2.86–3.06 (m, 2H), 3.26 (dd, J=5.4 Hz, 3.0 Hz, 1H), 3.36 (dd, J=9.8 Hz, 7.2 Hz, 1H), 3.80 (s, 3H), 3.82 (s, 3H), 3.87 (s, 3H), 4.24 (quint, J=6.2 Hz, 1H), 4.28 (dd, J=9.8 Hz, 3.0 Hz, 1H), 4.47–4.66 (m, 1H), 4.76–4.93 (m, 1H), 5.21 (s, 2H), 6.05 (dd, J=9.1 Hz, 7.1 Hz, 1H), 6.89 (d, J=8.8 Hz, 2H), 7.38 (d, J=8.8 Hz, 2H)

IR ν max (CHCl$_3$) cm$^{-1}$: 1776, 1717 MS m/z: 545[(M−I)$^+$], 1217[(2M−I)$^+$] [(M−I)$^+$] C$_{29}$H$_{45}$N$_2$O$_6$Si Calcd.: 545.3044 Found: 545.3039

EXAMPLE 3

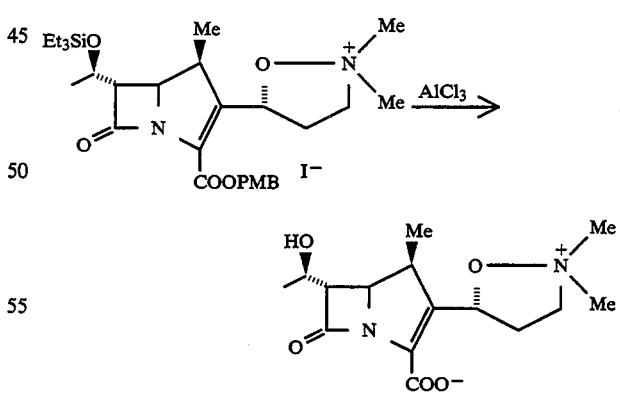

The iodide of (1S,6S)-2-((5R)-2,2-dimethyl-isoxazolidinio-5-yl)-1-methyl-6-((R)-1-triethylsilyloxyethyl)-1-carba-2-penem-3-carboxylic acid p-methoxybenzyl ester (1.13 g; 1.58 mmol; purity 94%) obtained in Example 2 was dissolved in a mixture of dichloromethane (9 ml) and nitromethane (3 ml). The obtained solution was cooled to about −60° C., and a solution of aluminum chloride (843 mg; 4 eq.) in anisole (3.5 ml) was added thereto. Then, the resultant solution was warmed to be about −15° C. over about 1.5 hours and stirred for 30 minutes at that temperature. The obtained reaction solution was diluted with dichloromethane, and a solution of sodium hydrogencarbonate (707 mg; 5.32 eq.) in water (10 ml) was added thereto. The resultant solution was stirred for about 10 minutes under ice cooling. Then, the reaction mixture was filtered, and the aqueous layer was separated, purified by a CHP-20 column chromatography and lyophilized to give (1S,6S)-6-((R)-1-hydroxyethyl)-2-((5R)-2,2-dimethylisoxazolidinio-5-yl)-1-methyl-1-carba-2-penem-3-carboxylate (301 mg). Yield starting from the monomethyl compound (i.e., the starting material in Example 2): 61%

$^1$H-NMR (D$_2$O, DOH=4.80 ppm) δ:1.15 (d, J=7.2 Hz, 3H), 1.27 (d, J=6.2 Hz, 3H), 2.61–2.93 (m, 2H), 3.35 (dq, J=9.4 Hz, 7.2 Hz, 1H), 3.47 (dd, J=6.2 Hz, 9.6 Hz, 1H), 3.60 (s, 6H), 4.06–4.34 (m, 4H), 5.98 (dd, J=9.7 Hz, 6.3 Hz, 1H)

IR ν max (KBr) cm$^{-1}$: 3400, 1750 UV λ max (H$_2$O) nm: 274 (ε=6800) Ms m/z: 311[(M+H)$^+$], 621[(2M+H)$^+$], 931[(3M+H)$^+$] [(M+H)$^+$] C$_{15}$H$_{23}$N$_2$O$_5$ Calcd.: 311.1606 Found: 311.1610

EXAMPLE 4

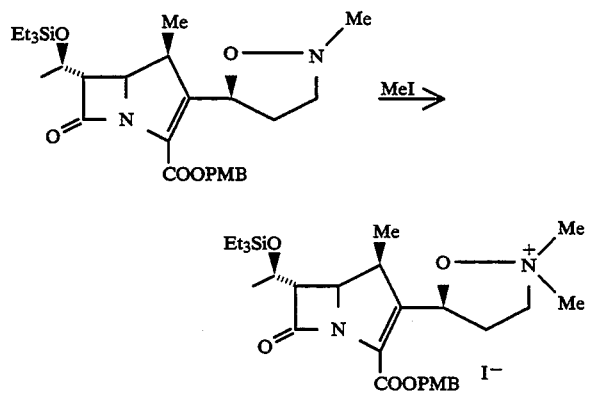

In the same manner as in Example 2, an iodide of (1S,6S)-2-((5S)-2,2-dimethylisoxazolidinio-5-yl)-1-methyl-6-((R)-1-triethylsilyloxyethyl)-1-carba-2-penem-3-carboxylic acid p-methoxybenzyl ester (6.6 g) was obtained from the (1S,6S)-1-methyl-2-((5S)-2-methylisoxazolidine-5-yl)-6-((R)-1-triethylsilyloxyethyl)-1-carba-2-penem-3-carboxylic acid p-methoxybenzyl ester (5 g; 9.42 mmol) obtained in Example 1. Yield: 100%. Purity: 96%.

$^1$H-NMR(CDCl$_3$) δ:0.58 (q, J=8.2 Hz, 6H), 0.93 (t, J=8.2 Hz, 9H), 1.24 (d, J=6.2 Hz, 3H), 1.27 (d, J=6.4 Hz, 3H), 2.57–2.84 (m, 1H), 3.00–3.19 (m, 1H), 3.19–3.38 (m, 2H), 3.81 (s, 3H), 3.91 (s, 3H), 3.94 (s, 3H), 4.22 (dd, J=10.2 Hz, 3.0 Hz;, 1H), 4.24 (quint, J=6.2 Hz, 1H), 4.50–4.83 (m, 2H), 5.23 (s, 2H), 5.91 (dd, J=10.0 Hz, 6.2 Hz, 1H), 6.89 (d, J=8.7 Hz, 2H), 7.38 (d, J=8.7 Hz, 2H)

IR ν max (CHCl$_3$) cm$^{-1}$: 1778, 1714 MS m/z: 545[(M−I)$^+$], 1217[(2M−I)$^+$] [(M−I)$^+$] C$_{29}$H$_{45}$N$_2$O$_6$Si Calcd.: 545.3044 Found: 545.3036

EXAMPLE 5

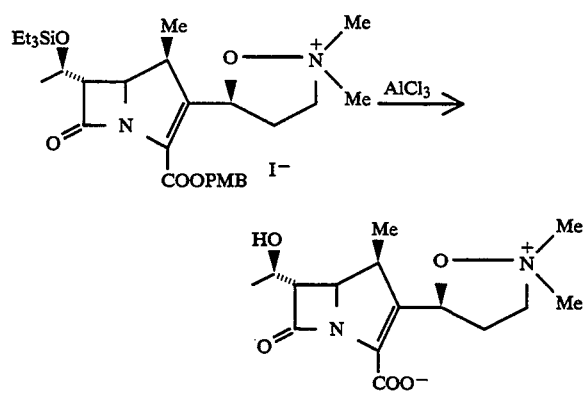

In the same manner as in Example 3, (1S,6S)-6-((R)-1-hydroxyethyl)-2-((5S)-2,2-dimethylisoxazolidinio-5-yl)-1-methyl-1-carba-2-penem-3-carboxylate (1.375 g) was obtained from the iodide of (1S,6S)-2-((5S)-2,2-dimethylisoxazolidinio-5-yl)-1-methyl-6-((R)-1-triethylsilyloxyethyl)-1-carba-2-penem-3-carboxylic acid p-methoxybenzyl ester (6.6 g; 9.42 mmol; purity: 96%) obtained in Example 4. Yield starting from the monomethyl compound: 47%.

$^1$H-NMR (D$_2$O, DOH=4.80 ppm) δ:1.23 (d, J=7.2 Hz, 3H), 1.30 (d, J=6.4 Hz, 3H), 2.59–3.13 (m, 2H), 3.29–3.47 (m, 1H), 3.50 (dd, J=5.1 Hz, 2.9 Hz, 1H), 3.63 (s, 6H), 4.08–4.37 (m, 4H), 5.91 (dd, J=9.9 Hz, 6.3 Hz, 1H)

IR ν max (KBr) cm$^{-1}$: 3500, 1750 UV λ max (H$_2$O) nm: 274 (ε=-5000), 225 (ε=5500) MS m/z: 311 [(M+H)$^+$], 621[(2M+H)$^+$], 931[(3M+H)$^+$] [(M+H)$^+$] C$_{15}$H$_{23}$N$_2$O$_5$ Calcd.: 311.1606 Found: 311.1600

EXAMPLE 6

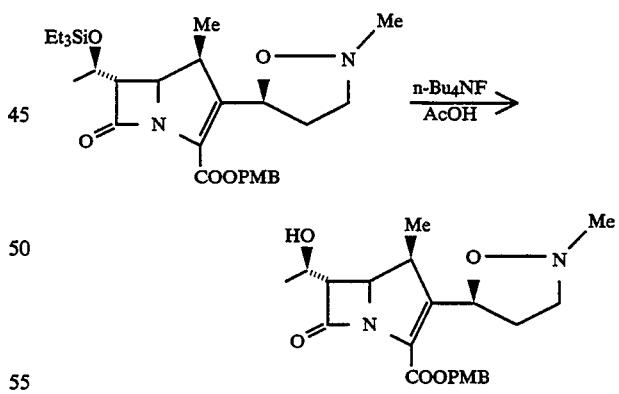

To a solution of (1S,6S)-1-methyl-2-((5S)-2-methylisoxazolidine-5-yl)-6-((R)-1-triethylsilyloxyethyl-1-carba-2-penem-3-carboxylic acid p-methoxybenzyl ester (116 mg; 0.22 mmol) obtained in Example 1 in tetrahydrofuran (1 ml) was added acetic acid (38 μl; 0.66 mmol) and a tetrahydrofuran solution (1.0M, 0.66 ml: 0.66 mmol) of tetrabutylammonium fluoride under ice cooling, and the resultant mixture was stirred for about 30 minutes. The obtained reaction mixture was poured into water-ethyl acetate, the organic layer was separated, end the aqueous layer was extracted with ethyl acetate. The ethyl acetate layer was combined, washed with a saturated aqueous solution of sodium hydrogencarbonate and saturated brine, dried over magnesium mullets and concentrated in vacuo. The residue was purified by the silica gel column chromatography (ethyl acetate) to give (1S,6S)-6-((R)-1-hydroxyethyl)-1-methyl-2-((5S)-2-methylisoxazolidine-5-yl)-1-carba-2-penem-3-carboxylic acid p-methoxybenzyl ester (70 mg). Yield: 77%.

$^1$H-NMR (CDCl$_3$) δ:1.24 (d, J=7.4 Hz, 3H), 1.33 (d, J=6.2 Hz, 3H), 1.70–2.12 (m, 1H), 2.28–2.52 (m, 1H), 2.56–2.86 (m, 1H), 2.66 (s, 3H), 3.19–3.60 (m, 2H), 3.25 (dd, J=6.6 Hz, 2.8 Hz, 1H), 3.80 (s, 3H), 4.15 (dd, J=9.8 Hz, 2.8 Hz, 1H), 4.23 (quint, J=6.4 Hz, 1H), 5.16 (ABq, J=12.1 Hz, 1H), 5.24 (ABq, J=12.1 Hz, 1H), 5.36–5.55 (m, 1H), 6.89 (d, J=8.7 Hz, 2H), 7.37 (d, J=8.7 Hz, 2H)

IR ν max (CHCl$_3$) cm$^{-1}$: 3424, 1767, 1712 MS m/z: 417[(M+H)$^+$], 833[(2M+H)$^+$] [(M+H)$^+$] C$_{22}$H$_{29}$N$_2$O$_6$ Calcd.: 417.2024 Found: 417.2031

EXAMPLE 7

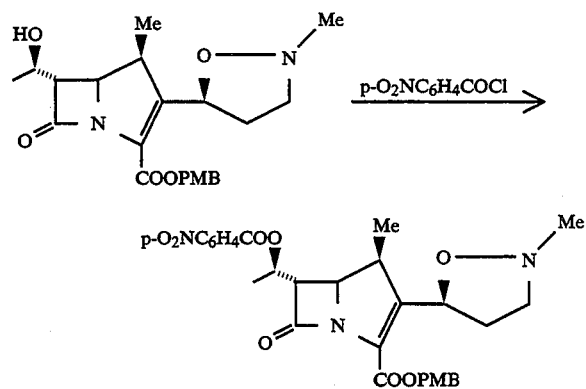

To the solution of (1S,6S)-6-((R)-1-hydroxyethyl)-1-methyl-2-((5S)-2-methylisoxazolidine-5-yl)-1-carba-2-penem-3-carboxylic acid p-methoxybenzyl ester (188 mg; 0.45 mmol) obtained in Example 6 in dichloromethane (4 ml) were added trimethylamine (94 μl; 0.68 mmol), 4-nitrobenzoylchloride (126 mg; 0.68 mmol) and 4-(dimethylamino)pyridine (28 mg; 0.23 mmol) at −40°C., and the obtained mixture was stirred for about 2 hours. The reaction mixture was poured into water-dichloromethane, the organic layer was separated, and the aqueous layer was extracted with dichloromethane. The dichloromethane layer was combined, washed with saturated brine, dried over magnesium sulfate and concentrated in vacuo. The residue was purified by the silica gel column chromatography (toluene:ethyl acetate=1:1) to give (1S, 6S)-1-methyl-2-((5S)-2-methylisoxazolidine-5-yl)-6-((R)-1-p-nitrobenzoyloxyethyl)-1-carba-2-penem-3-carboxylic acid p-methoxybenzyl ester (227 mg). Yield: 89%. m.p.: 131°–132° C. The configuration of a carbon atom attached to the 2-position of the penem ring was determined to be S by an X ray crystal analysis.

$^1$H-NMR (CDCl$_3$) δ:1.29 (d, J=7.4 Hz, 3H), 1.53 (d, J=6.2 Hz, 3H), 1.78–2.14 (m, 1H), 2.28–2.52 (m, 1H), 2.58–2.90 (m, 1H), 2.67 (s, 3H), 3.16–3.63 (m, 2H), 3.55 (dd, J=6.4 Hz, 2.8 Hz, 1H), 3.78 (s, 3H), 4.22 (dd, J=9.7 Hz, 2.8 Hz, 1H), 5.20 (s, 2H), 5.35–5.60 (m, 1H), 5.54 (quint, J=6.4 Hz, 1H), 6.85 (d, J=8.6 Hz, 2H), 7.34 (d, J=8.6 Hz, 2H), 8.15 (dd, J=6.6 Hz, 2.6 Hz, 2H), 8.22 (dd, J=6.6 Hz, 2.6 Hz, 2H)

IR ν max (CHCl$_3$) cm$^{-1}$: 1774, 1720, 1528, 1341 Elemental analysis (C$_{29}$H$_{31}$N$_3$O$_9$) Calcd.: C, 61.59, H, 5.52, N, 7.43 Found: C, 61.46, H, 5.64, N, 7.44

EXAMPLE 8

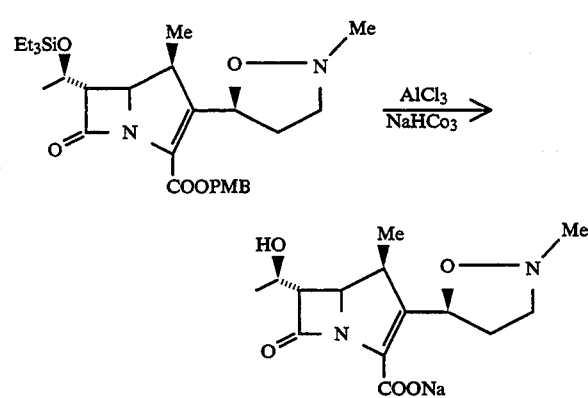

The (1S,68)-1-methyl-2-((5S)-2-methylisoxazolidine-5-yl)-6-((R)-1-triethylsilyloxyethyl)-1-carba-2-penem-3-carboxylic acid p-methoxybenzyl ester (260 mg; 0.49 mmol) obtained in Example 1 was dissolved in a mixture of dichloromethane (3 ml) and nitromethane (1 ml). To the resultant solution, a solution of aluminum chloride (261 mg; 4 eq.) in anisole (1 ml) was added dropwise in an atmosphere of nitrogen at −60° C. The resultant solution was warmed to −15° C. over about 1 hour, and stirred for about 1 hour. Then, the resultant solution was diluted with dichloromethane, diluted with a solution of sodium hydrogencarbonate (568 mg; 13.8 eq.) in water (6 ml), and stirred for about 10 minutes under ice cooling. The obtained solution was filtered, and the filtrate was washed with dichloromethane, and purified by the CHP-20P column chromatography to give sodium (1S,6S)-6-((R)-1-hydroxyethyl)-1-methyl-2-((5S)-2-methylisoxazolidine-5-yl)-1-carba-2-penem-3-carboxylate salt (102 mg). Yield: 65%.

$^1$H-NMR (CDCl$_3$) δ:1.23 (d, J=7.6 Hz, 3H), 1.30 (d, J=6.4 Hz, 3H), 2.04–2.28 (m, 1H), 2.43–3.51 (m, 5H), 2.78 (s, 3H), 4.17 (dd, J=9.7 Hz, 2.5 Hz, 1H), 4.25 (quint, J=6.4 Hz, 1H), 5.26 (t, J=8.0 Hz, 1H)

The carbapenem compounds obtained in Examples 3, 5 and 8 were evaluated for antimicrobial activity, the integrated value of a concentration in blood (Area Under the Curve: AUC), recovery from urine and decomposition by human kidney dehydropeptidase-1 by using imipenem, meropenem and cephalosporin derivatives (A) and (B) as controls. The results are shown in Table 1.

TABLE 1

| | Compound Obtained in Example 3 | Compound Obtained in Example 5 | Compound Obtained in Example 8 | Imipenen | Meropenen | Cephalosporin (A) | Cephalosporin (B) |
| --- | --- | --- | --- | --- | --- | --- | --- |
| MIC | | | | | | | |
| Staphylococcus aureus 209P (γ/ml) | 0.0125 | 0.0125 | 0.1 | 0.0125 | 0.10 | 0.78 | 0.20 |

TABLE 1-continued

| | Compound Obtained in Example 3 | Compound Obtained in Example 5 | Compound Obtained in Example 8 | Imipenen | Meropenen | Cephalosporin (A) | Cephalosporin (B) |
|---|---|---|---|---|---|---|---|
| Entercoccus SR1004 ($\gamma$/ml) | 0.78 | 0.78 | — | 1.56 | 6.25 | — | — |
| Pseudomonas aeruginosa SR1012 ($\gamma$/ml) | 0.78 | 1.56 | — | 1.56 | 0.78 | — | — |
| Intravenous Injection to Mouse | | | | | | | |
| Concentration in Blood ($\gamma$/ml) | 36.3 | — | — | 20.6 | 13.7 | — | — |
| AUC | 19.0 | — | — | 8.8 | 5.2 | — | — |
| Recovery from Urine (%) | 63.7 | — | — | 31.3 | 16.6 | — | — |
| Intravenous Injection to Monkey | | | | | | | |
| AUC | 35.2 | — | — | 13.3 | 17.2 | — | — |
| Recovery from Urine (%) | 42.2 | — | — | 32.1 | 45.7 | — | — |
| Decomposition by Human Kidney Dehydropeptidase −1 (%) | 97 | — | — | 73 | 87 | — | — |

<Evaluation Method>

1) MIC (Minimal Inhibitory Concentration) ($\gamma$/ml):
Antimicrobial activity was evaluated by using MIC.

2) Concentration in Blood ($\gamma$/ml):
Each compound was intravenously injected into a mouse, and the concentration in the blood 15 minutes after the injection was measured.

3) Recovery from Urine (%):
Each compound was intravenously injected into a mouse and a monkey, and the content in the urine 24 hours after the injection was measured. A rate of recovery was obtained from the content.

The results in Table 1 show that the carbapenem derivatives obtained in Examples 3, 5 and 8 exhibit excellent antimicrobial activity against Gram-positive bacteria and Gram-negative bacteria as compared with imipenem, meropenem and cephaloporin derivatives (A) and (B). Moreover, the carbapenem derivatives obtained in Examples 3, 5 and 8 have a high concentration in blood 15 minutes after the injection, a high recovery rate from urine 24 hours after the injection and a low hydrolysis rate in the body.

Various other modifications will be apparent to and can be readily made by those skilled in the art without departing from the scope and spirit of this invention. Accordingly, it is not intended that the scope of the claims appended hereto be limited to the description as eat forth herein, but rather that the claims be broadly construed.

What is claimed is:

1. A carbapenem derivative represented by Formula I:

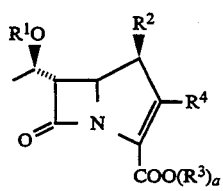

(I)

wherein $R^1$ is a hydrogen or a hydroxy protecting group; $R^2$ is substituted or non-substituted lower alkyl; $R^3$ is hydrogen, an inorganic base, an organic base selected from the group consisting of triethylamine salt, pyridine salt, picoline salt, ethanolamine salt, triethanolamine salt, dicyclohexylamine salt, N,N'-dibenzylethylenediamine salt and dibenzylamine salt, or a carboxy protecting group; a is 0 or 1; and $R^4$ is a group represented by any of the following Formulae II through V:

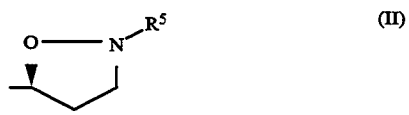

(II)

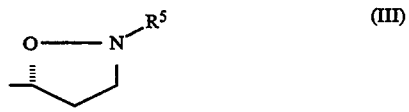

(III)

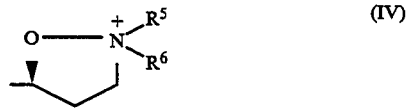

(IV)

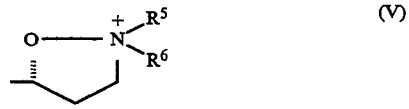

(V)

wherein $R^5$ and $R^6$ are independently substituted or non-substituted lower alkyl, or the salts thereof.

2. A carbapenem derivative according to claim 1, wherein $R^1$ is hydrogen; $R^2$ is methyl; $R^3$ is hydrogen, an inorganic base, an organic base selected from the group consisting of triethylamine salt, pyridine salt, picoline salt, ethanolamine salt, triethanolamine salt, dicyclohexylamine salt, N,N'-dibenzylethylenediamine salt and dibenzylamine salt, or a carboxy protecting group; a is 0 or 1; and $R^4$ is a group represented by any of the following Formulae IIa, IIIa, IVa and Va:

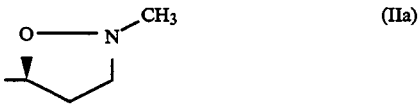

(IIa)

-continued

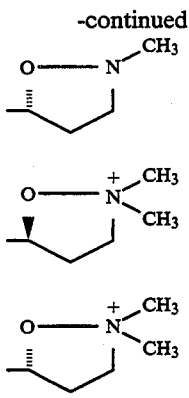

3. An anti-bacterial composition comprising the carbapenem derivative of claim 1 as an active ingredient.

4. A method for combatting bacteria in mammals by applying a bacteriostatically effective amount of the carbapenem derivative of claim 1.

5. An anti-bacterial composition comprising the carbapenem derivative of claim 2 as an active ingredient.

6. A method for combatting bacteria in mammals by applying a bacteriostatically effective amount of the carbapenem derivative of claim 2.

7. The carbapenem derivative of claim 1, wherein $R^4$ is a group represented by any of the formulae II and III, wherein $R^5$ is substituted or non-substituted lower alkyl, or the salts thereof.

8. The carbapenem derivative of claim 1, wherein $R^4$ is a group represented by any of the formulae IV and V, wherein $R^5$ and $R^6$ are independently substituted or non-substituted lower alkyl, or the salts thereof.

9. The carbapenem derivative of claim 1, wherein $R^3$ is an inorganic base.

10. The carbapenem derivative of claim 1, wherein the inorganic base is selected from the group comprising alkali metal, salts, alkaline-earth metal salts and ammonium salt.

11. The carbapenem derivative of claim 1, wherein $R^3$ is an organic base selected from the group consisting of triethylamine salt, pyridine salt, picoline salt, ethanolamine salt, triethanolamine salt, dicyclohexylamine salt, N,N'-dibenzylethylenediamine salt and dibenzylamine salt.

12. The carbapenem derivative of claim 2, wherein $R^4$ is a group represented by any of the formulae IIa and IIIa.

13. The carbapenem derivative of claim 2, wherein $R^4$ is a group represented by any of the formulae IVa and Va.

14. The carbapenem derivative of claim 2, wherein $R^3$ is an inorganic base.

15. The carbapenem derivative of claim 2, wherein the inorganic base is selected from the group consisting of alkali metal salts, alkaline-earth metal salts and ammonium salt.

16. The carbapenem derivative of claim 2, wherein $R^3$ is an organic base selected from the group consisting of triethylamine salt, pyridine salt, picoline salt, ethanolamine salt, triethanolamine salt, dicyclohexylamine salt, N,N'-dibenzylethylenediamine salt and dibenzylamine salt.

* * * * *

UNITED STATES PATENT AND TRADEMARK OFFICE
CERTIFICATE OF CORRECTION

PATENT NO. : 5,338,733

DATED : August 16, 1994

INVENTOR(S) : Mitsuru Imuta et al.

It is certified that error appears in the above-identified patent and that said Letters Patent is hereby corrected as shown below:

Column 14, line 64, insert --▼-- below "O" of $Et_3SiO$.

Column 15, line 5, insert --▼-- below "O" of $Et_3SiO$.

Column 15, line 13, insert --▼-- below "O" of $Et_3SiO$.

Column 20, line 19, change "$NaHCo_3$" to --$NaHCO_3$--.

Column 20, line 30, change "(1S,68)" to --(1S,6S)--.

Signed and Sealed this

Twenty-ninth Day of November, 1994

Attest:

BRUCE LEHMAN

*Attesting Officer*     *Commissioner of Patents and Trademarks*